United States Patent [19]

Contois

[11] Patent Number: 4,468,444
[45] Date of Patent: Aug. 28, 1984

[54] PYRYLIUM-SENSITIZED LEUCO BASE PHOTOCONDUCTIVE COMPOSITIONS AND ELEMENTS CONTAINING NAPHTHALENE BIS-DICARBOXIMIDE COMPOUNDS

[75] Inventor: Lawrence E. Contois, Webster, N.Y.

[73] Assignee: Eastman Kodak Company, Rochester, N.Y.

[21] Appl. No.: 468,830

[22] Filed: Apr. 21, 1983

[51] Int. Cl.$^3$ .............................................. G03G 5/06
[52] U.S. Cl. ........................................ 430/72; 430/73; 430/74; 430/83
[58] Field of Search ...................... 430/73, 74, 83, 72

[56] References Cited

U.S. PATENT DOCUMENTS

| | | | |
|---|---|---|---|
| 3,542,547 | 11/1970 | Wilson | 94/1.6 |
| 4,286,036 | 8/1981 | Hendriksma | 430/79 X |
| 4,301,226 | 11/1981 | Contois et al. | 430/72 |
| 4,423,126 | 12/1983 | Klijanowicz et al. | 430/9 |

*Primary Examiner*—John D. Welsh
*Attorney, Agent, or Firm*—Torger N. Dahl

[57] ABSTRACT

Photoconductive compositions and elements comprising arylalkane photoconductors and pyrylium sensitizers are stabilized against adverse leuco base color shifts into the ultraviolet to blue spectral region by the incorporation of certain 1,4,5,8-naphthalene bis-dicarboximide compounds. The compositions and elements are particularly suited for electrophotographic image formation and thereafter for contact printing of the image onto sensitive material by ultraviolet or blue transmission through the composition or element.

7 Claims, No Drawings

PYRYLIUM-SENSITIZED LEUCO BASE PHOTOCONDUCTIVE COMPOSITIONS AND ELEMENTS CONTAINING NAPHTHALENE BIS-DICARBOXIMIDE COMPOUNDS

The present invention relates to photoconductive compositions containing arylalkane photoconductors, pyrylium sensitizers and cyclic bis-dicarboximide sensitizers.

Photoconductive materials and elements consist of varied formats, combinations of layers, and degrees of transparency or opacity in order to meet particular commercial needs. One such element is adapted for charging, exposure and development to form a toned image, followed by second-generation printing of an ultraviolet- or blue-sensitive material by appropriate light exposure through the toned image-bearing element. To this end, the element must be adequately sensitive to the radiation employed during formation of the toned image and yet transmit light in the ultraviolet to blue wavelength band to facilitate the second-generation printing.

An important class of photoconductive compounds includes arylalkane leuco bases as shown in U.S. Pat. Nos. 3,542,547 issued Nov. 24, 1970, to C. V. Wilson and 4,301,226 issued Nov. 17, 1981, to L. E. Contois et al. These photoconductors have at least one major absorption peak at wavelengths below 400 nm. Leuco bases, however, are sometimes unstable, tending to form their corresponding dye derivatives upon exposure to ambient conditions. To prevent the undesired dye formation, the arylalkane leuco bases of U.S. Pat. Nos. 3,542,547 and 4,301,226 are stabilized, such as by substitution in ortho positions of two phenyl groups of the molecule. The resulting stabilized leuco bases are thus useful as photoconductors and do not have a tendency to form undesired dye density when exposed to ambient conditions, which would decrease or prevent the desired transmission of ultraviolet or blue light in second-generation printing.

Compositions containing the arylalkane leuco bases of U.S. Pat. Nos. 3,542,547 and 4,301,226, moreover, can be spectrally sensitized with pyrylium or thiapyrylium salts. In particular, the 4-aminobenzo[b]pyrylium and 4-aminobenzo[b]thiapyrylium salts described in U.S. Pat. No. 3,577,235 are commonly employed, as such salts are relatively transparent to radiation in the ultraviolet to blue region. Unfortunately, compositions containing pyrylium or thiapyrylium salts of U.S. Pat. No. 3,577,235 in combination with arylalkane leuco bases increase the production of adverse color density at high ambient humidity and temperature (for example, 80 percent relative humidity and 33° C.), causing reduced transparency to ultraviolet and blue light. Accordingly, the use of such compositions for second-generation ultraviolet- to blue-light printing in such environments requires unacceptable high exposure levels for effective printing. It would be desirable to minimize or eliminate such adverse color density changes in pyrylium-sensitized, photoconductive compositions containing arylalkane leuco bases.

In accordance with the present invention, such color density increases are minimized or eliminated by incorporating into the photoconductive composition a 1,4,5,8-naphthalene bis-dicarboximide corresponding to the structure:

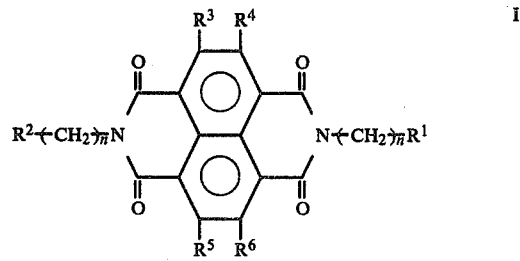

wherein:
$R^1$ and $R^2$, which may be the same or different, represent aryl, such as phenyl or naphthyl, or aryl substituted with alkyl, alkoxy, perfluoroalkyl or perfluoroalkoxy groups having 2 to 20 alkyl carbon atoms; sulfonyl; sulfone; sulfonamide; nitrile; or nitro groups;

$R^3$, $R^4$, $R^5$ and $R^6$, which may be the same or different, represent hydrogen, alkyl having 1 to 4 carbon atoms, alkoxy having 1 to 4 carbon atoms, or halogen;
and n is 0 to 3.

Photoconductive compositions according to the present invention, therefore, comprise an electrically insulating polymer binder containing an arylalkane leuco base, a 4-aminobenzo[b]pyrylium or 4-aminobenzo[b]thiapyrylium sensitizer and a 1,4,5,8-naphthalene bis-dicarboximide corresponding to Structure I above. The defined composition absorbs little or no (i.e., transmits most) radiation within the 400- to 450-nm-wavelength region of the electromagnetic spectrum, preferably within the 410- to 430-nm region, and so is eminently suited for use in a contact printing process employed light exposure in these wavelengths.

Representative 1,4,5,8-naphthalene bis-dicarboximides employed in the defined composition include the compounds listed in Table 1.

TABLE 1

A.

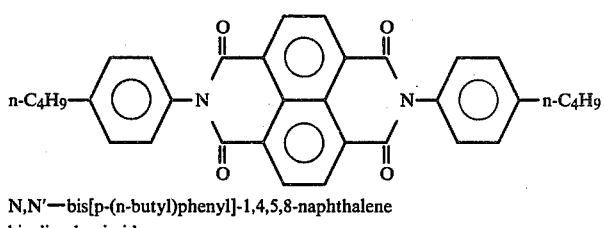

N,N'—bis[p-(n-butyl)phenyl]-1,4,5,8-naphthalene bis-dicarboximide

TABLE 1-continued

B.

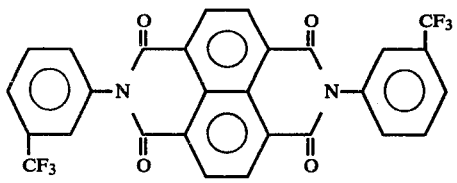

N,N'—bis(m-trifluoromethylphenyl)-1,4,5,8-naphthalene bis-dicarboximide

C.

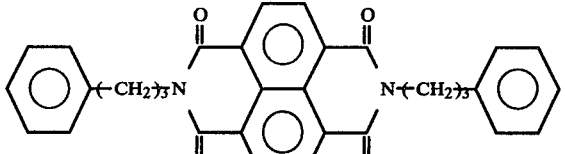

N,N'—bis(3-phenylpropyl)-1,4,5,8-naphthalene bis-dicarboximide

D.

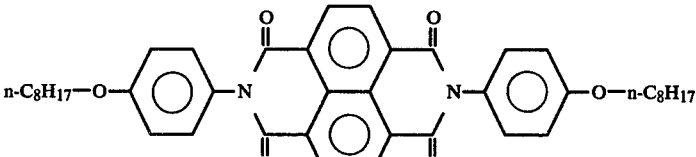

N,N'—bis[p-(n-octyloxy)phenyl]-1,4,5,8-naphthalene bis-dicarboximide

The amount of dicarboximide employed can vary widely. A useful guide in selecting an appropriate concentration is first to determine the extent of the leuco base color shift in the photoconductive composition defined above in the absence of the dicarboximide. The leuco base color shift is that amount of light absorbed by a composition in the ultraviolet to blue region of the spectrum in terms of optical density after the composition has been exposed for at least 30 minutes to a converged exposure of black-light ultraviolet radiation and photoflood radiation at 50 percent relative humidity. The ultraviolet exposure source comprised two General Electric Company F15T8-BL (15 watt, black light) tubes and the photoflood source comprised a Westinghouse Company 300-watt reflector bulb. The light sources were spaced approximately 12.7 cm from the composition. Dicarboximide of choice is added to the composition in an amount sufficient to decrease the leuco base color shift. In this regard we have found, for example, that dicarboximide in a concentration of at least 1 percent, by weight of the total composition on a solvent-free basis, can reduce the leuco base color shift by 50 percent or more. A preferred dicarboximide concentration range is 0.2 to 3 weight percent.

In the defined photoconductive composition, arylalkane leuco bases are the principal photoconductive constituent. These compounds are disclosed in U.S. Pat. No. 3,542,547 above and have the structure:

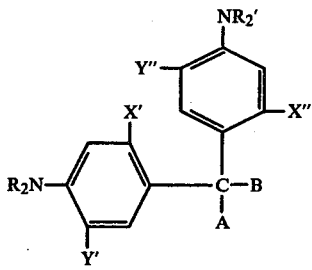

wherein:
each of R and R' is selected from the group consisting of hydrogen, alkyl and aralkyl having 1 to 4 carbon atoms in the alkyl group;
each of X' and X" is selected from the group consisting of alkyl having 1 to 4 carbon atoms, alkoxy having 1 to 4 carbon atoms, hydroxyl and halogen;
each of Y' and Y" is selected from the group consisting of alkyl having 1 to 4 carbon atoms, alkoxy having 1 to 4 carbon atoms, hydroxyl, halogen and hydrogen; and
each of A and B is:
  (1) hydrogen, with the proviso that A and B are not both hydrogen;
  (2) aryl such as phenyl, α-naphthyl, β-naphthyl, 9-anthryl and substituted derivatives thereof wherein the substituent is dialkylamino, alkylamino, amino, alkyl, alkoxy, hydroxyl or halogen;
  (3) an aliphatic alkyl group having 1–18 carbon atoms, e.g., methyl, ethyl, propyl, butyl, isobutyl, octyl, dodecyl, etc., including a substituted alkyl group having 1–18 carbon atoms;
  (4) a cycloalkyl group having 4–8 carbon atoms in the cyclic nucleus, e.g., cyclobutyl, cyclohexyl, cyclopentyl, etc., including a substituted cycloalkyl group; or (5) a cycloalkenyl group having 4–8 carbon atoms in the cyclic nucleus, e.g., cyclohex-3-enyl, cyclopent-3-enyl, cyclobut-2-enyl, cyclohex-2-enyl, etc., including a substituted cycloalkenyl group.

Representative Formula I stabilized arylmethane leuco-base photoconductors are set forth in Table 2 below.

Table 2

(1) 4,4'-bis(diethylamino)-2,2'-dimethyltriphenylmethane
(2) 4,4'-bis(diethylamino)-2,5-dichloro-2',2''-dimethyltriphenylmethane
(3) 4,4'-bis(diethylamino)-2,2'-dimethyldiphenyl-α-naphthylmethane
(4) 2',2''-dimethyl-4,4',4''-tris(dimethylamino)triphenylmethane
(5) 4',4''-bis(diethylamino)-4-dimethylamino-2',2'',5,5''-tetramethyltriphenylmethane
(6) 4',4''-bis(diethylamino)-2-chloro-2',2''-dimethyl-4-dimethylaminotriphenylmethane
(7) 4',4''-bis(diethylamino)-4-dimethylamino-2,2',2''-trimethyltriphenylmethane
(8) 4',4''-bis(dimethylamino)-2-chloro-2',2''-dimethyltriphenylmethane
(9) 4',4''-bis(dimethylamino)-2',2''-dimethyl-4-methoxytriphenylmethane
(10) 4,4'-bis(benzylethylamino)-2,2''-dimethyltriphenylmethane
(11) 4,4'-bis(diethylamino)-2,2',5,5''-tetramethyltriphenylmethane
(12) 4,4'-bis(diethylamino)-2,2'-diethoxytriphenylmethane
(13) 4,4'-bis(diethylamino)-2,2'-dimethyldiphenyl-β-naphthylmethane
(14) 4,4'-bis(diethylamino)-2,2'-dimethyldiphenyl-9-anthrylmethane
(15) 4,4',4''-trisdiethylamino-2,2',2''-trimethyltriphenylmethane
(16) 1,1-bis(4-N,N-diethylamino-2-chlorophenyl)-2-phenylethane
(17) 1,1-bis(4-N,N-diethylamino-2-methoxyphenyl)-2-phenylethane
(18) bis(4-N,N-diethylaminophenyl)cyclopent-2-enylmethane
(19) bis(4-N,N-diethylamino-2-methylphenyl)cyclobut-2-enylmethane
(20) 1,1-bis(4-N,N-diethylaminophenyl)-3-phenylpropane
(21) 1,1-bis(4-N,N-diethylaminophenyl)-2-phenylethane
(22) 1,1-bis(N,N-diethylaminophenyl)butane
(23) bis(4-N,N-diethylaminophenyl)cyclohexylmethane
(24) 1,1-bis(4-N,N-diethylaminophenyl)-2-methylpropane
(25) 1,1-bis(4-N,N-diethylaminophenyl)heptane
(26) bis(4-N,N-diethylaminophenyl)cyclohex-3-enylmethane
(27) 1,1-bis(4-N,N-diethylaminophenyl)-2-ethylhexane
(28) 1,1-bis(4-N,N-diethylamino-2-methylphenyl)-3-phenylpropane
(29) 1,1-bis(4-N,N-diethylamino-2-methylphenyl)-2-phenylethane
(30) 1,1-bis(4-N,N-diethylamino-2-methylphenyl)butane
(31) 1,1-bis(4-N,N-diethylamino-2-methylphenyl)cyclohexylmethane
(32) 1,1-bis(4-N,N-diethylamino-2-methylphenyl)-2-methylpropane
(33) 1,1-bis(4-N,N-diethylamino-2-methylphenyl)butane
(34) bis(4-N,N-diethylamino-2-methylphenyl)cyclohex-3-enylmethane
(35) bis(4-N,N-diethylamino-2-methylphenyl)-4-methylphenylmethane
(36) bis(4-diethylamino)-1,1,1-triphenylethane
(37) bis(4-diethylamino)tetraphenylmethane
(38) 1,1-bis(4-N,N-diethylaminophenyl)cyclohexane
(39) 1,1-bis(4-di-p-tolylaminophenyl)cyclohexane
(40) 1,1-bis(4-di-p-tolylaminophenyl)-2-methylpropane
(41) 1,1-bis(4-N,N-diethylaminophenyl)-4-methylcyclohexane
(42) 1,1-bis(4-N,N-dipropylaminophenyl)cyclohexane
(43) 1,1-bis(4-N,N-diethylaminophenyl)-1-(4-methylphenyl)ethane
(44) 4,4'-bis(diethylamino)-4'',4'''-dichlorotetraphenylmethane
(45) 4,4'-bis(dipropylamino)tetraphenylmethane
(46) 4,4'-bis(diethylamino)-4''-isopropyl-2,2'-dimethylyltriphenylmethane Particularly useful compositions of the present invention comprise crystallization-inhibiting mixtures of two or more of the above leuco base photoconductors as disclosed in U.S. Pat. No. 4,301,226 issued Nov. 17, 1981, to L. E. Contois et al. A preferred crystallization-inhibiting mixture comprises three leuco base photoconductors: bis(4-N,N-diethylamino-2-methylphenyl)-4-methylphenylmethane, 1,1-bis(4-N,N-diethylamino-2-methylphenyl)-2-methylpropane and 4,4'-bis(diethylamino)-2,2'-dimethyltriphenylmethane.

The total amount of arylalkane leuco-base photoconductor in the defined composition may vary widely, but preferably ranges from about 5 to about 40 weight percent based on the solvent-free weight of the layer.

The photoconductive compositions of the present invention are spectrally sensitized with effective amounts of a 4-aminobenzo[b]pyrylium or 4-aminobenzo[b]thiapyrylium salt. These salts correspond to the following structure:

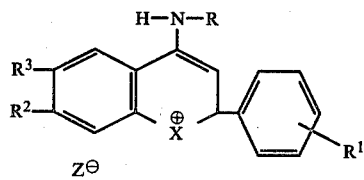

wherein:

X is sulfur or oxygen.

Z is an anion such as perchlorate, fluoroborate, sulfonate, periodate, or p-toluenesulfonate.

R is alkyl having from 1 to 10 carbon atoms or aryl. Alkyl includes unsubstituted or substituted alkyl. Representative alkyl groups include methyl, ethyl, isopropyl, n-butyl, pentyl, octyl, decyl, cyclopentyl or cyclohexyl. Preferred substituents on the alkyl group include aryl such as phenyl or naphthyl.

$R^1$ is hydrogen, alkyl having 1 to 4 carbon atoms, or alkoxy having 1 to 4 carbon atoms. Representative alkyl and alkoxy groups include methyl, ethyl, isopropyl, butyl, methoxy, ethoxy, propoxy or butoxy.

Each of $R^2$ and $R^3$, when taken separately, represents a hydrogen atom and, when taken together, are attached to adjacent carbon atoms and represents the atoms necessary to form a fused aromatic ring such as a benzo ring.

Effective amounts of the sensitizer represented by Structure III can vary widely in order to increase the speed of the composition of the present invention. The optimum concentration in any given case will vary with the specific photoconductor and sensitizing compound used. Substantial speed gains can be obtained where a sensitizer according to Structure III is added in a concentration range from about 0.0001 to about 30 percent based on the weight of the composition on dry basis. A preferred sensitizer concentration range is from about 0.005 to about 5.0 percent.

Compositions of the present invention are incorporated into an electrically insulating binder and coated as photoconductive layers on an electrically conductive support to form a photoconductive element. The elements so formed are employed in electrophotographic processes to form toned images in a conventional manner.

Preferred electrically insulating binders for use in preparing the photoconductive layers are film-forming, hydrophobic polymeric binders having fairly high dielectric strength. Materials of this type comprise styrene-butadiene copolymers; silicone resins; styrene-alkyd resins; silicone-alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals) such as poly(vinyl butyral); polyacrylic and polymethacrylic esters such as poly(methyl methacrylate), poly(n-butyl methacrylate), poly(isobutyl methacrylate); polystyrene; nitrated polystyrene; polymethylstyrene; isobutylene polymers; polyesters such as poly[ethylene-co-alkylenebis(alkyleneoxyaryl)-phenylenedicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloarylates; poly(ethylene-co-neopentyl terephthalate); and vinyl acetate such as poly(vinyl-m-bromobenzoate-co-vinyl acetate). Combinations of these materials may be used. The layers may also contain a surfactant or coating aid, if desired.

Suitable supporting materials for the photoconductive layers of the present invention can include any electrically conducting supports. Examples include conducting papers, aluminum-paper laminate, metal foils such as aluminum and zinc foils; metal plates such as aluminum, copper, zinc, brass and galvanized plates, vapor-deposited metal layer (silver, nickel, aluminum) on conventional film supports such as cellulose acetate, poly(ethylene terephthalate), polystyrene and the like.

A useful conducting support can be prepared by coating a transparent film support such as poly(ethylene terephthalate) with a layer containing a semiconductor dispersed in a resin. A suitable conducting coating can be prepared from the sodium salt of a carboxyester lactone of a maleic anhydride-vinyl acetate copolymer or cuprous iodide or the like.

Useful techniques for forming electrophotographic elements and using such elements are described in greater detail in U.S. Pat. Nos. 4,301,226, 3,245,833, 3,267,807 and 3,007,901.

The following examples are provided to aid in the understanding of the present invention.

Preparation of
N,N'-bis[p-(n-butyl)phenyl]-1,4,5,8-naphthalenebis(-dicarboximide)

(Table 1, Compound A)

A mixture of 30 g (0.11M) of 1,4,5,8-naphthalenetetracarboxylic dianhydride and 33.4 g (0.22M) of p-(n-butyl)aniline in 500 mL of phenyletherbiphenyl-eutectic (bp 258° C.) was azeotropically refluxed for 15 hr. After cooling to room temperature, the crystallized solid was filtered and washed with ether until the filtrate turned colorless, to give approximately 50 g of crude Compound A. This was dissolved in 800 mL of hot chloroform; some activated charcoal was added and the mixture cooled to room temperature. The mixture was filtered over diatomaceous earth and the clear, light brown filtrate was concentrated on a steam bath to approximately 400 mL from which 40 g of product was obtained. Further purification was achieved by recrystallization from 2 L of p-dioxane to give 31 g (53%) of pure Compound A as a slightly yellowish solid, mp 358°–360° C.

Preparation of
N,N'-bis(m-trifluoromethylphenyl)-1,4,5,8-naphthalenebis(dicarboximide)

(Table 1, Compound B)

A mixture of 4.1 g (0.015M) of 1,4,5,8-naphthalenetetracarboxylic dianhydride and 4.9 g (0.03M) of m-(trifluoromethyl)aniline in 150 mL of phenylether-biphenyl-eutectic mixture was azeotropically refluxed overnight. The precipitated solid, on cooling, was filtered, washed with ether and dissolved in 500 mL of methylene chloride. The insoluble black impurities were removed by filtration over diatomaceous earth and the clear filtrate reduced in volume in a rotary evaporator. The residue was recrystallized from 250 mL of acetonitrile to give 2.5 g of pure Compound B: mp 349°–350° C.

Preparation of
N,N'-bis[p-(n-octyloxy)phenyl]-1,4,5,8-naphthalenebis(dicarboximide)

(Table 1, Compound D)

A mixture of 3.1 g (0.0114M) of 1,4,5,8-naphthalenetetracarboxylic dianhydride and 5.07 g (0.0229M) of p-(n-octyloxy)aniline in 150 mL of phenylether-biphenyl-eutectic mixture was azeotropically refluxed overnight. The precipitated solid obtained on cooling was filtered, washed thoroughly with ether and boiled in 300 mL of 1% KOH with stirring for 1 hr. The insoluble solid was filtered, washed with water, air-dried and recrystallized from 400 mL of toluene to give 4.25 g (55%) of pure Compound D: mp 346°–348° C.

EXAMPLE 1

This illustrates the use of a dicarboximide compound from Table 1 to reduce the leuco base color shift in a photoconductive composition of the present invention.

A photoconductive element comprising a photoconductive composition on a transparent conductive polyethylene terephthalate film support was prepared following the procedure of Example 7 in U.S. Pat. No. 4,301,226 described above. The element employed differed from that of U.S. Pat. No. 4,301,226 in the following respects: tri-p-tolylamine was excluded from the composition, the sensitizer was 4-[N-butylamino-2-(p- methoxyphenyl)benzo[b]pyrylium tetrafluoroborate, and the pyrylium dye concentration was 0.7 percent, by weight of the solvent-free composition. This element was designated as the control element.

In a second element, 1%, by weight of the photoconductive layer, of Compound A, Table 1, and 0.35 percent of the pyrylium dye employed in the control element were incorporated as dissolved constituents into the photoconductive layer.

The leuco base color shift, as defined herein, of each element was determined by treating each element to a 2.5-hr converged exposure of a tungsten photoflood source and a black-light ultraviolet-radiation source at 50% relative humidity.

The optical density of the control element at 420 nm before treatment was 0.19 OD; after treatment, the optical density of the control element at the same wavelength increased to 0.41 OD.

The optical density (OD) at 420 nm of the element containing dicarboximide Compound A, however, did not increase significantly after treatment. The optical density of this element before treatment was 0.19 OD and after treatment was 0.21 OD.

Although the invention has been described in considerable detail with particular reference to certain preferred embodiments thereof, variations and modifications can be effected within the spirit and scope of the invention.

I claim:

1. A photoconductive composition comprising at least one arylalkane leuco base photoconductor, a 4-aminobenzo[b]pyrylium or 4-aminobenzo[b]-thiopyrylium sensitizer and a 1,4,5,8-naphthalene bis-dicarboximide compound in effective amounts to reduce the leuco base color shift of said composition, said naphthalene bis-dicarboximide having the structure:

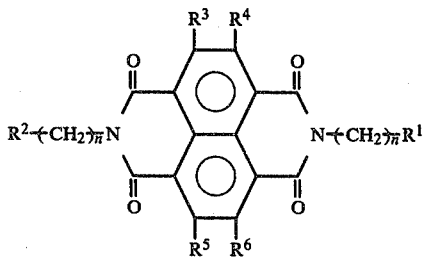

wherein:
R$^1$ and R$^2$, which may be the same or different, represent aryl, or aryl substituted with alkyl, alkoxy, perfluoroalkyl or perfluoroalkoxy groups having 2 to 20 alkyl carbon atoms; sulfonyl; sulfone; sulfonamide; nitrile; or nitro groups;
R$^3$, R$^4$, R$^5$ and R$^6$, which may be the same or different, represent hydrogen, alkyl having 1 to 4 carbon atoms, alkoxy having 1 to 4 carbon atoms, or halogen;
and n is 0 to 3.

2. A composition as in claim 1 wherein said dicarboximide compound is selected from the group consisting of N,N'-bis[p-(n-butyl)phenyl]-1,4,5,8-naphthalene bis-dicarboximide, N,N'-bis(m-trifluoromethylphenyl)-1,4,5,8-naphthalene bis-dicarboximide, N,N'-bis(3-phenylpropyl)-1,4,5,8-naphthalene bis-dicarboximide and N,N'-bis[p-(n-octyloxy)phenyl]1,4,5,8-naphthalene bis-dicarboximide.

3. A composition as in claims 1 or 2 wherein the concentration of said dicarboximide compound is at least 1 percent by weight of said composition on a solvent-free basis.

4. A composition as in claim 1 wherein said leuco base photoconductor has the structure:

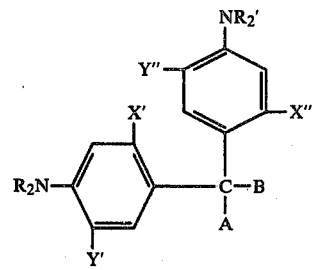

wherein:
each of R and R' is selected from the group consisting of hydrogen, alkyl and aralkyl having 2 to 4 carbon atoms in the alkyl group;
each of X' and X" is selected from the group consisting of alkyl having 1 to 4 carbon atoms, alkoxy having 1 to 4 carbon atoms, hydroxyl and halogen;
each of Y' and Y" is selected from the group consisting of alkyl having 1 to 4 carbon atoms, alkoxy having 1 to 4 carbon atoms, hydroxyl, halogen and hydrogen; and
each of A and B is:
(1) hydrogen, with the proviso that A and B are not both hydrogen;
(2) aryl and substituted derivatives thereof wherein the substituent is dialkylamino, alkylamino, amino, alkyl, alkoxy, hydroxyl or halogen;
(3) an aliphatic alkyl group having 1–18 carbon atoms;
(4) a cycloalkyl group having 4–8 carbon atoms in the cyclic nucleus; or
(5) a cycloalkenyl group having 4–8 carbon atoms in the cyclic nucleus;
and said sensitizer has the structure:

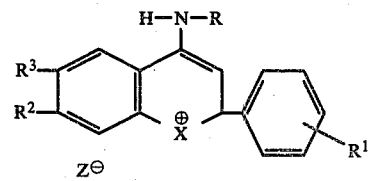

wherein:
X is sulfur or oxygen;
Z is an anion such as perchlorate, fluoroborate, sulfonate, periodate or p-toluenesulfonate;
R is alkyl having from 1 to 10 carbon atoms or aryl;
R$^1$ is hydrogen, alkyl having 1 to 4 carbon atoms, or alkoxy having 1 to 4 carbon atoms;
each of R$^2$ and R$^3$, when taken separately, represents a hydrogen atom and, when taken together, is attached to adjacent carbon atoms and represents the atoms necesary to form a fused aromatic ring such as a benzo ring.

5. A composition as in claim 4 comprising the three leuco base photoconductors bis(4-N,N-diethylamino-2-methylphenyl)-4-methylphenylmethane, 1,1-bis(4-N,N- diethylamino-2-methylphenyl)-2-methylpropane and 4,4'-bis(diethylamino)-2,2'-dimethyltriphenylmethane.

6. A composition as in claim 5 wherein said sensitizer is 4-[N-butylamino]-2-p-methoxyphenyl)benzo[b]pyrylium tetrafluoroborate and said dicarboximide is N,N-bis[p-(n-butyl)phenyl]-1,4,5,8-naphthalene bis dicarboximide.

7. A photoconductive element comprising an electrically conducting support and a layer of the photoconductive composition of claims 1, 2, 3, 4, 5 or 6 overlying said support.

* * * * *